(12) United States Patent
Greter et al.

(10) Patent No.: US 9,308,506 B2
(45) Date of Patent: Apr. 12, 2016

(54) MIXING APPARATUS HAVING DISPLAY FOR PRESSURE CHANGE

(75) Inventors: Andy Greter, Baar (CH); Martin Veid, Weggis (CH); Rochus Stockli, Buochs (CH); Wilhelm A. Keller, Merlischachen (CH)

(73) Assignee: MEDMIX SYSTEMS AG, Rotkreuz (CH)

( * ) Notice: Subject to any disclaimer, the term of this patent is extended or adjusted under 35 U.S.C. 154(b) by 117 days.

(21) Appl. No.: 13/145,053

(22) PCT Filed: Dec. 2, 2009

(86) PCT No.: PCT/CH2009/000384
§ 371 (c)(1),
(2), (4) Date: Jul. 18, 2011

(87) PCT Pub. No.: WO2010/083616
PCT Pub. Date: Jul. 29, 2010

(65) Prior Publication Data
US 2011/0273954 A1 Nov. 10, 2011

(30) Foreign Application Priority Data

Jan. 21, 2009 (CH) .......................................... 89/09

(51) Int. Cl.
| | |
|---|---|
| *B01F 15/02* | (2006.01) |
| *B01F 11/00* | (2006.01) |
| *B01F 13/00* | (2006.01) |
| *B01F 15/00* | (2006.01) |
| *A61B 19/00* | (2006.01) |
| *A61F 2/30* | (2006.01) |
| *A61F 2/46* | (2006.01) |
| *B01F 13/06* | (2006.01) |
| *A61B 17/88* | (2006.01) |

(52) U.S. Cl.
CPC .......... *B01F 15/0205* (2013.01); *B01F 11/0082* (2013.01); *B01F 13/002* (2013.01); *B01F 13/0023* (2013.01); *B01F 15/00071* (2013.01); *B01F 15/00155* (2013.01); *B01F 15/00162* (2013.01); *B01F 15/00188* (2013.01); *B01F 15/0203* (2013.01); *B01F 15/0206* (2013.01); *B01F 15/0226* (2013.01);
(Continued)

(58) Field of Classification Search
CPC .................... B01F 2215/0029; A61B 17/8802
USPC ...................................... 366/139, 142, 163.1
See application file for complete search history.

(56) References Cited

U.S. PATENT DOCUMENTS 3,877,682 A * 4/1975 Moss ............................ 366/132
4,376,439 A * 3/1983 Lauterjung .................... 604/319
(Continued)

FOREIGN PATENT DOCUMENTS

| DE | 200 05 333 U1 | 7/2001 |
|---|---|---|
| EP | 1 076 776 B1 | 2/2001 |

(Continued)

*Primary Examiner* — David Sorkin
*Assistant Examiner* — Abbas Rashid
(74) *Attorney, Agent, or Firm* — Sughrue Mion, PLLC (57) ABSTRACT

A mixing apparatus for mixing at least two components comprises a mixing chamber having a first component and at least one component chamber having a further component. The component chamber is connected to the mixing chamber by a feed line. A negative pressure device generates a negative pressure in the mixing chamber in the starting position. By activating the negative pressure device, the pressure is equalized, whereby the further component is transferred into the mixing chamber. A display apparatus is provided at the component chamber to display a pressure change in the component chamber. The display apparatus is preferably formed by elastic bellows provided at one end of the component chamber, which is disposed opposite of the end of the component chamber following the feed line.

17 Claims, 4 Drawing Sheets

(52) U.S. Cl.
CPC .... B01F 15/0278 (2013.01); *A61B 2017/8838* (2013.01); *A61B 2019/464* (2013.01); *A61F 2/30742* (2013.01); *A61F 2002/30561* (2013.01); *A61F 2002/4666* (2013.01); *A61F 2002/4685* (2013.01); *B01F 13/06* (2013.01); *B01F 15/00506* (2013.01); *B01F 15/0266* (2013.01)

(56) References Cited

U.S. PATENT DOCUMENTS

| | | | | |
|---|---|---|---|---|
| 4,721,390 | A | * | 1/1988 | Lidgren ................... 366/139 |
| 5,279,550 | A | * | 1/1994 | Habib et al. .............. 604/38 |
| 6,120,174 | A | * | 9/2000 | Hoag et al. ............... 366/139 |
| 6,176,607 | B1 | * | 1/2001 | Hajianpour ............... 366/139 |
| 6,210,031 | B1 | * | 4/2001 | Murray ..................... 366/139 |
| 6,254,268 | B1 | * | 7/2001 | Long ........................ 366/139 |
| 6,435,705 | B1 | * | 8/2002 | Long ........................ 366/139 |
| 7,073,936 | B1 | * | 7/2006 | Jonsson .................... 366/139 |
| 2003/0155381 | A1 | | 8/2003 | Chan |

FOREIGN PATENT DOCUMENTS

| | | |
|---|---|---|
| EP | 1 525 864 A1 | 4/2005 |
| WO | 97/07748 A1 | 3/1997 |
| WO | 99/06140 A1 | 2/1999 |
| WO | 2005/018831 A1 | 3/2005 |
| WO | 2008/009143 A1 | 1/2008 |
| WO | 2010/012114 A1 | 2/2010 |

* cited by examiner

MIXING APPARATUS HAVING DISPLAY FOR PRESSURE CHANGE

CROSS REFERENCE TO RELATED APPLICATION

This application is a National Stage of International Application No. PCT/CH2009/000384 filed Dec. 2, 2009, claiming priority based on Swiss Patent Application No. 00089/09, filed Jan. 21, 2009, the contents of all of which are incorporated herein by reference in their entirety.

TECHNICAL FIELD

The present invention relates to a mixing apparatus for mixing at least two components, in particular a mixing apparatus for mixing products for medical applications, for example bone cement.

PRIOR ART

In various technical fields, a product which is provided for further processing should not be produced from various components by mixing until directly before said product is used. This may be necessary since the product changes its state immediately after mixing, for example hardens or disintegrates into various constituents. In medical technology, products of this type which cannot be stored in the application state thereof are known, for example, in pharmaceuticals, or are known, for example, from the production of medicinal adhesives or bone cement. The product is generally composed of at least two components, wherein generally one component is present as a solid and a further component as a liquid. Shortly before the application, the liquid is mixed with the solid and the processing product produced in this manner is processed directly at the intended location thereof.

For example, WO 97/07748 discloses a mixing system of this type. A solid component is accommodated in a first container to which a second container can be connected and, in the process, establishes a liquid connection. An ampule, for example, containing a liquid component can be inserted into the second container. The second container can be rotated relative to the first container, as a result of which an opening mechanism is actuated which opens the ampule in the second container such that the liquid component can be conducted out of the ampule via the liquid connection into the first container. To assist the diversion of the liquid component, a vacuum which can be generated in the first container via a connector can be applied to the container system. It is ensured by means of the difference in pressure between the interior of the ampule and the vacuum in the container system that the liquid is fully emptied out of the ampule.

In the case of the mixing apparatus according to the prior art, the application of the vacuum to the container system can be checked by monitoring the switching on or off of the vacuum-generating device. If the vacuum device is switched on, it should be possible to assume that a vacuum is applied at least in the first container. However, it is not possible to check whether vacuum has also been generated in the second container or even in the ampule. It is possible that the liquid connection is blocked and therefore the vacuum cannot be generated in the second container. Furthermore, it is not possible to check whether the ampule has actually been opened and therefore the liquid component was able to pass into the first container because of the vacuum.

US 2003/0155381 likewise discloses, in FIGS. 13-16, a mixing apparatus in which a monomer component is transported out of a component container into a mixing apparatus by application of a vacuum. The monomer component is accommodated in a glass ampule. The glass ampule is located in an ampule holder and is displaceable in the longitudinal direction therein. At the lower end of the ampule holder there is a wedge onto which the ampule tip can be pushed in order to break the latter off. A plunger which is guided in a sealing manner in the ampule holder is arranged above the ampule. In order to transfer the monomer component into the mixing container, a vacuum is generated in the mixing container and, as a result, also in the ampule container. The plunger of the ampule holder is pulled vertically downward by the air pressure and presses the ampule onto the wedge, as a result of which the ampule tip breaks off. The monomer component is subsequently sucked out of the ampule by the vacuum. It can be determined by monitoring the position of the plunger whether a vacuum is actually present.

While this apparatus in principle makes it possible to determine whether there is a vacuum in the ampule holder, it is not entirely simple to arrive at said determination without any doubts, since the plunger is moved by the vacuum into the ampule holder and, as a result, is no longer visible when functioning correctly. The user is therefore forced to make an indirect conclusion regarding the correct functioning when determining that the plunger is no longer visible. This is disadvantageous since the plunger could also not be visible for other reasons, for example, because it has been forgotten to insert the plunger. This has an adverse effect on the functional reliability of the apparatus.

It is an object of the present invention to provide a mixing apparatus for mixing at least two components, in which the presence of a pressure change in the mixing system or/and the emptying of a component chamber into a mixing chamber can be reliably checked and which is simple to handle and has a simple construction.

SUMMARY OF THE INVENTION

A mixing apparatus for mixing at least two components according to the present invention has a mixing chamber with a first component, and at least one component chamber with a further component which differs from the first component, said component chamber being connected or being able to be connected to the mixing chamber via a feed line. The mixing chamber is preferably of cylindrical design and is filled, for example to half the volume, with the first component. If, for example, bone cement is provided as the mixing product, the powdery component can be provided in the mixing chamber and the mixing liquid can be provided in the at least one component chamber. The mixing chamber with the powder component, and the component chamber can be permanently stored separately from each other. A mixer which is movable relative to the mixing chamber is preferably provided in the mixing chamber. The mixer may be designed, for example, as a stirring element which is fastened to a plunger rod which is mounted in the interior of the mixing chamber so as to be movable in the longitudinal direction of the chamber. The mixing chamber is then preferably closed off at one end by a stopper, in which the plunger rod of the mixer is able to be guided in a sliding manner. An opening to which the feed line for the component chamber is connected is then provided at the opposite end of the mixing chamber. In the stored state, the mixing chamber can be closed and only opened and connected to the feed line prior to production of the mixture. A filter or screen can be provided at the opening to the mixing chamber.

In the case of the production of a conventional bone cement, it is sufficient to provide a single component chamber next to the mixing chamber. In principle, however, it is also possible to connect more than one component chamber containing a further component or else the same component as in the first component chamber to the mixing chamber via a teed line. The component chamber is preferably likewise of cylindrical design. The further component can be accommodated either directly in the component chamber or can be provided in a component container which can be inserted into the component chamber.

Furthermore, the mixing apparatus is provided with a negative pressure device, in particular a vacuum device, which can generate a negative pressure in the mixing chamber. When the negative pressure device is activated, there is therefore a lower pressure in the mixing chamber than in the component chamber. A vacuum is preferably roughly generated in the mixing chamber. The negative pressure device is connected for this purpose to the mixing chamber via a connection which preferably lies in a region of the chamber in which component particles are not located. In the case of an upright cylindrical mixing chamber, for example, the first component is located in a lower part of the chamber and the connection for the negative pressure device is located in an upper part of the chamber. Upon activation of the negative pressure device, the negative pressure propagates from the mixing chamber through the feed line into the component chamber or the component chambers.

By activation of the negative pressure device, the further component is transported, or sucked, from the at least one component chamber into the mixing chamber inter alia because of the equalization of pressure between the component chamber and the mixing chamber. A liquid component can also be transferred from the component chamber into the mixing chamber at least partially because of the equalization of a height difference of the liquid columns in the mixing chamber and the component chamber.

It is possible, but not necessary, to provide a closure device which, in a starting position of the mixing apparatus according to the invention, closes the feed line between the mixing chamber and the at least one component chamber, or the feed line to the component. The closure device can be provided in the feed line, for example, by a valve which can be brought from a closed into an open position, for example, by means of manual actuation. However, the closure device may also be coupled to a component container accommodated in the component chamber. The component container is mounted in the component chamber in such a manner that, in the closed state of said component container, it closes, or blocks, the feed line, and, in the open state thereof, opens up the feed line. The opening of the closure device is therefore directly coupled to the opening of the component container in the component chamber. If the component container is provided, for example, by an ampule, the closure device can be opened, for example, by severing the ampule head. Furthermore, the closure device can also be formed directly by the component in the component chamber. By means of the component, part of the volume of the component chamber is cut off such that the chamber part upstream of the component is open to the feed line and the chamber part downstream of the component is separated from the feed line.

In order to open the component container, for example, in the form of an ampule, an opening device can be provided, for example, on the component chamber. The opening device can be located substantially in the interior of the component chamber but can be actuated from an outside of the component chamber. The opening device is preferably designed according to WO2010/012114 dated Jul. 14, 2009. However, it is also possible to use other devices for opening the component container, such as the devices also known, for example, from the prior art.

According to the present invention, a display apparatus which indicates a pressure change in the component chamber is provided on at least one of the component chambers on the mixing apparatus. By means of the display apparatus according to the invention it is possible to monitor the negative pressure, which is generated by the negative pressure device, in the component chamber. At the same time, it can therefore be checked that the feed line is open. A pressure reduction in the component chamber is preferably checked with the display apparatus. It can therefore be determined that the further component has been transported, or sucked, from the component chamber into the mixing chamber by an equalization of the pressure between the lower pressure in the mixing chamber and the higher pressure in the component chamber. The display therefore likewise serves as a means of monitoring the emptying of the component chamber.

The display apparatus is formed by an elastic region of the component chamber. The chamber can thus be formed, for example, by a solid material cylinder which has an elastic material only in a predetermined region. The elastic region may be provided, for example, in the circumferential wall of the cylinder, but is preferably arranged at one end as a termination of the cylinder. Said end is preferably opposite the other cylinder end with the opening to the feed line to the mixing chamber. The elastic region is particularly preferably formed by a bellows which can be placed onto the cylinder end. The bellows can be designed as an expansion bellows or else as a balloon bellows. Upon a pressure change in the component chamber, the bellows contracts in the event of a pressure reduction and the bellows is inflated in the event of a pressure increase.

In the starting position of the mixing apparatus, the display apparatus is in a first position. By activation of the negative pressure device, a pressure difference can be produced between the mixing chamber and the at least one component chamber. After the pressure has been equalized, i.e. reduced, in the component chamber, the display apparatus is in a second position which indicates that a pressure change has taken place in the component chamber. The display apparatus therefore changes from a starting position to a display position by means of the pressure change. The display apparatus preferably comprises a color marking for the colored differentiation of the starting position from the display position. In principle, however, it is also possible to mark the positions by means of letters, numbers or other signs.

In order to produce the desired mixture with a mixing apparatus according to the invention, first of all the component from the component chamber can be at least partially introduced into the feed line and also into the mixing chamber, for example by opening of an ampule in the component chamber or by opening of a closure device between the feed line and component chamber. The feed line is therefore closed by the component. Subsequently, a negative pressure can be produced in the mixing chamber relative to the component chamber by means of the negative pressure device. By equalization of the pressure, the component remaining in the feed line and the component chamber is first of all sucked into the mixing chamber and subsequently pressure equalization takes place in the component chamber, said pressure equalization activating the display apparatus, i.e. placing the latter from the starting position into the display position.

As an alternative, in a mixing apparatus according to the invention, a negative pressure can also be generated first of all in the mixing chamber if a closure device blocking the feed line to the component chamber, or to the component chamber part with the display device, is provided. Then, by opening of the closure device, on the one hand, the component can be transferred from the component chamber into the mixing chamber and, on the other hand, the pressure between the mixing chamber and component chamber can be equalized, with the display apparatus being displaced from the starting position into the display position.

As soon as the display apparatus has changed from the starting position into the display position for displaying the pressure change, the user can be certain that the at least one component chamber has been emptied and the further component has been transferred by the feed line into the mixing chamber. The user can now mix the components with one another using the mixer of the mixing chamber. Subsequently, a discharge nozzle can be placed onto the mixing chamber over the opening and the mixture can be discharged through the discharge nozzle, for example, by means of advancing a stopper in the mixing chamber.

The display apparatus is preferably designed in such a manner that a change in the volume of the component chamber, on which the display apparatus is provided, can be displayed. In this embodiment, in the event of a pressure reduction in the chamber by means of the equalization of pressure between the mixing chamber and the component chamber, the volume of the component chamber is reduced at the same time.

In preferred embodiments, the display apparatus is arranged at the component chamber end which is opposite the end to which the feed line is connected. The component chamber therefore has the display apparatus at one end and an outlet, which leads into the feed line to the mixing chamber, at an end opposite said end. The component is preferably provided in the chamber between the display apparatus and the feed line. It is ensured by means of this embodiment of the display apparatus that there is a pressure change over the entire volume of the component chamber. As soon as a pressure equalization takes place between the mixing chamber and the component chamber, said pressure equalization will extend over the entire volume of the component chamber and will therefore also trigger the actuation of the display apparatus.

The display apparatus is preferably movable counter to an elastic force from the starting position into the display position which differs therefrom. The elastic force can be produced, for example, by the deformation of a material or by a spring device provided in the display apparatus. Upon a pressure reduction in the component chamber, the elastic force therefore has to be overcome in order to be able to move the display apparatus from the starting position into the display position. As soon as the pressure is equalized with the ambient pressure after a pressure change and an associated movement of the display apparatus from the starting position into the display position, the display apparatus is moved back again into the starting position from the display position by the prestressing of the elastic force. This is possible, for example, if the negative pressure device is deactivated or if the component chamber is separated from the overall system of mixing chamber, feed line and component chamber such that the pressure can be equalized with the surroundings through the chamber opening. The elastic force of the material or of the spring device forms a counterforce to the force which acts on the display apparatus upon a pressure change in the component chamber. Therefore, slight pressure changes in the component chamber do not yet cause any change in the display apparatus, since the force of said pressure changes is not sufficient to overcome the elastic force.

According to the present invention, the display apparatus is preferably provided removably on the component chamber. This advantageously makes it possible to provide access to the component chamber in order, for example, to accommodate the further component, or a component container with the further component, in the chamber. The display apparatus can subsequently be attached again to the component chamber. If the display apparatus is provided, for example, by means of an elastic bellows, the latter can be widened, for example, at the opening thereof, in order to pull said bellows over an opening on the component cylinder. Once placed on, the opening of the bellows is contracted until an airtight connection is produced between the component chamber and the bellows. In the relaxed state, the bellows is then in a starting position and can be moved into a display position counter to the elastic force thereof by means of a pressure change. In an embodiment of a mixing apparatus according to the present invention, a base unit is provided in which at least part of the feed line is provided and which has connections for connecting the mixing chamber and the at least one component chamber to the feed line, or to said part of the feed line. The mixing chamber and the component chamber are preferably arranged releasably on the connections. The mixing chamber, the at least one component chamber and the base unit therefore form a kit which forms the mixing apparatus. For the mixing of at least two components, a user can therefore attach the mixing chamber and the at least one component chamber via the connections of the base unit and can connect the mixing chamber to the negative pressure device. By activation of the negative pressure device, the second component can therefore be conducted into the mixing chamber by equalization of the pressure between the component chamber and the mixing chamber. The components can be mixed by means of the movable mixer, the mixing chamber can be removed from the base unit and the mixture is ready for use.

BRIEF DESCRIPTION OF THE DRAWINGS

Preferred embodiments of the invention are illustrated below with reference to the drawings which serve merely for explanation and should not be interpreted as limiting. Features of the invention which become obvious from the drawings should be considered individually and in every combination as belonging to the disclosure of the invention. In the drawings.

Figure 1:
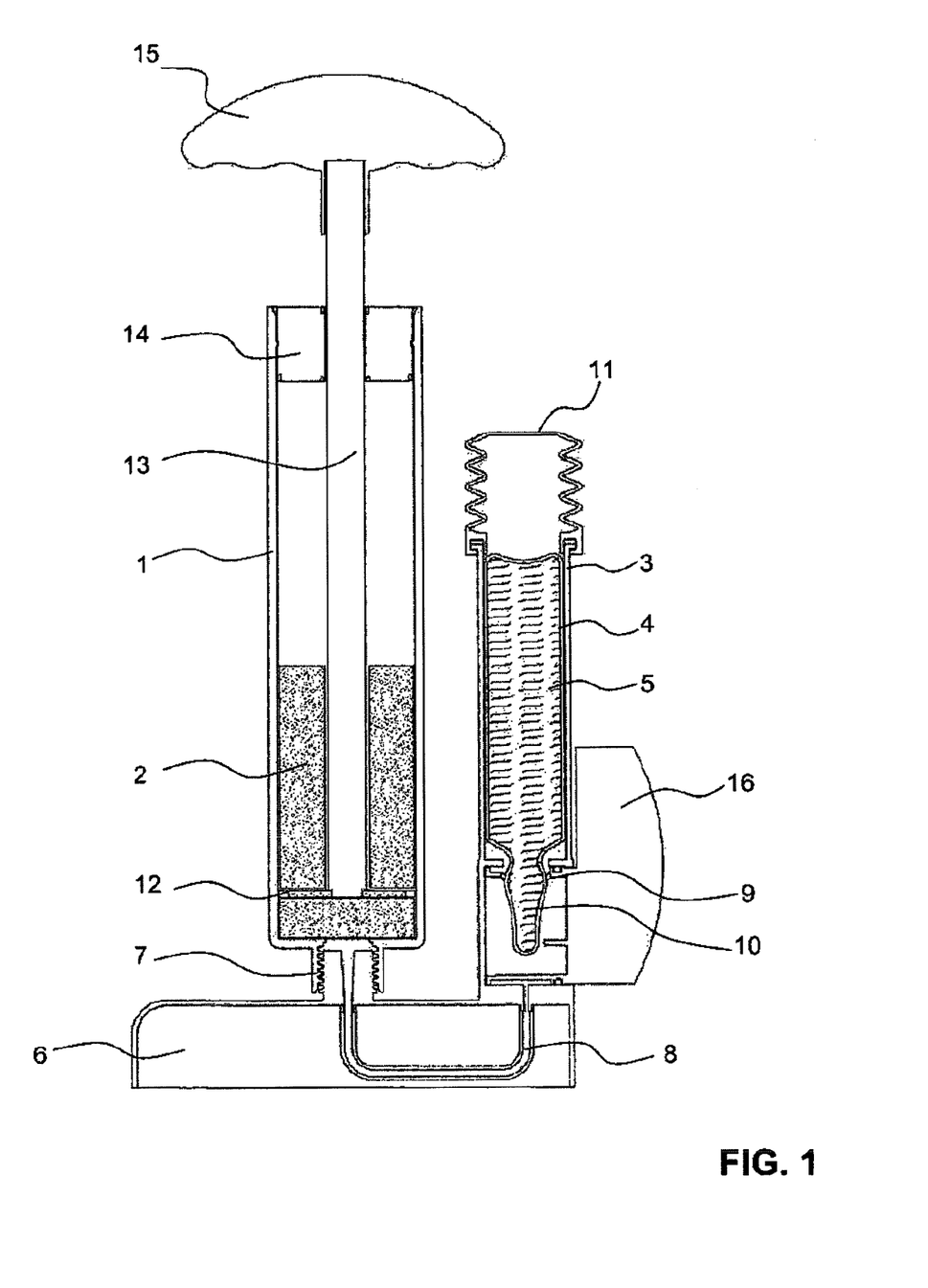
FIG. 1 shows a longitudinal section through a first embodiment of a mixing apparatus according to the present invention in a starting position.

FIG. 1 shows a first embodiment of a mixing apparatus according to the present invention for mixing at least two components. The mixing apparatus has a mixing chamber 1 with a first component 2 and a component chamber 3 in which a component container 4 with a second component 5 is accommodated. The mixing chamber 1 and the component chamber 3 are fastened on a base unit 6. The mixing chamber 1 is attached releasably to the base unit 6 by means of a screw connection 7, in this case a bayonet fastener.

In the exemplary embodiment shown, the component chamber 3 is connected fixedly to the base unit and, in the present case, is formed integrally with the base unit. As an alternative, however, it is also possible to also connect the component chamber releasably to the base unit. The component chamber 3 is connected to the mixing chamber 1 via a feed line 8. The feed line 8 runs through the base part 6 and leads out of the base unit on the upper side of the base unit. The feed line extends into the screw connection 7 and, when the mixing chamber is placed on, produces with the mixing chamber 1 a fluid connection to the interior of the mixing chamber. At the other end, the feed line 8 leads into the interior of the component chamber 3. A filter which can retain the first component 2, for example a powder, in the mixing chamber, can be provided over the opening of the mixing chamber 1 to the feed line 8. A further filter which can retain impurities or splinters which may be produced, for example, by the opening of a component container in the form of an ampule, can be provided over the opening of the component chamber 3 to the feed line 8. The mixing apparatus is shown in a starting position in which the components are scored separately from one another in their respective chambers.

On the rear side of the mixing chamber according to FIG. 1, the upper part of the mixing chamber has a connector (not shown) for a negative pressure device which can generate a negative pressure in the mixing chamber relative to the component chamber.

The component container 4 in the form of an ampule is held in the interior of the component chamber 3 by flexible lips 9 which are provided on an inwardly protruding flange of the component chamber. The flexible lips 9 protrude into the interior of the component chamber 3 in a lower region in the vicinity of the outlet of the component chamber 3 to the feed line 8. At one end, the component container 4 has a container head 10 with which said component container projects through the flexible lips 9 of the component chamber and is held by said lips. The flexible lips 9 can be formed, for example, from elastic material, such as rubber, which bears against the container head 10 around the entire circumference thereof and therefore supports the component container 4 in the component chamber 3. In the starting position according to FIG. 1, the mixing apparatus is in an inoperative position in which it can be stored even for a prolonged period of time.

It is conceivable for the flexible lips 9 to act as sealing lips and to form a type of closure device between the mixing chamber and the component chamber. The flexible lips 9 divide the component chamber into two regions, one region upstream of the closure device and one region downstream of the closure device, in which region the ampule body is located. In the starting position according to FIG. 1, the flexible lips 9 bear tightly against the container head 10 such that the closure device is in a closed position.

A display apparatus in the form of an elastically deformable bellows 11, which can display a pressure change in the component chamber 3, is provided on the component chamber 3. The bellows 11 is located at an open end of the cylinder of the component chamber 3, which end is opposite the end which faces the feed line 8. The bellows 11 is pulled with an opening over the opening in the component chamber 3 and tightly closes off the opening in the component chamber. The bellows 11 is designed in the manner of a concertina, i.e. it has, on the outer circumferential surface thereof, a zigzag-like, predetermined series of folds along which the bellows can be compressed in the longitudinal direction, with the folds coming to lie on one another. In the position shown in FIG. 1, the bellows is in a relaxed position, i.e. in the starting position.

The mixing chamber 1 is provided with a mixer 12 which is movable relative to the mixing chamber. The mixer 12 is attached to a plunger rod 13 which protrudes out of the mixing chamber 1 at that end of the mixing chamber 1 which is opposite the end in the direction of the feed line 8. The plunger rod 13 is mounted movably in a stopper 14 which tightly closes off the mixing chamber at this end. As soon as the second component 5 has been fed into the mixing chamber 1, the plunger rod 13 can be grasped at a handle 15 and the mixer 12 can be moved into and out of the mixing chamber 1 by the plunger rod 13 being slid in and out and rotated, in order to mix the components with one another. The mixing preferably takes place when the mixing chamber 1 is placed onto the base unit 6. However, the mixing chamber 1 may also be removed from the base unit 6 prior to the mixing, in which case the opening 7 has to be closed again for the mixing.

Figure 2:
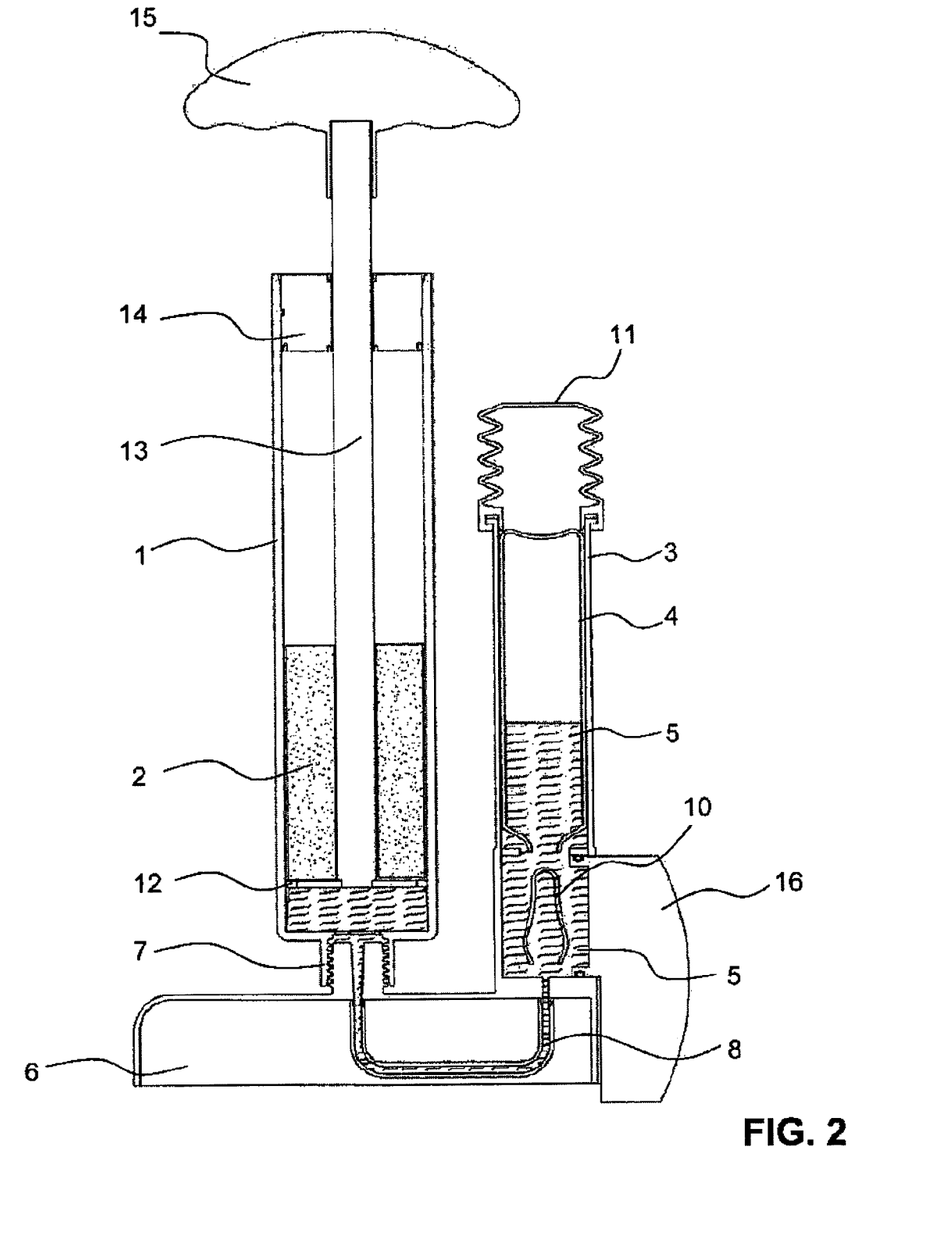
FIG. 2 shows a longitudinal section through the embodiment according to FIG. 1 with the closure device open.

FIG. 2 shows the mixing apparatus according to FIG. 1 in a state in which the component container 4 has been opened. For this purpose, a rotary lever 16 is arranged laterally on the component chamber 3 and is connected to an opening device in the interior of the component chamber 3 in such a manner that, by rotation of the rotary lever 16, the container head 10 is severed from the component container 4. FIG. 2 shows the rotary lever 16 in a downwardly rotated position in which the container head 10 has been severed such that the second component 5 emerges from the component container 4. With regard to the configuration of the opening device for the component container 4, reference is made to the description in the application WO2010/0122114 dated Jul. 14, 2009, which has already been mentioned, and its disclosure regarding an apparatus for opening an ampule is hereby incorporated into the disclosure for the present invention. In the design of the rotary lever 16, care has to be taken to ensure that the transition to the component chamber 3 is sealed.

By the opening of the component container 4, some of the component 5 flows into the feed line 8 and some even into the mixing chamber 1. The transfer takes place, inter alia, by means of the different height of the liquid columns of the component 5 in the component chamber 3 and the mixing chamber 1. A residual gas volume is provided above the component 5 in the component container 4. When the component container 4 is opened, or when the container head 10 is broken off, the gas expands such that, owing to the expansion, a pressure is exerted on the component 5 and the latter is pushed into the feed line 8.

After the opening of the component container, the negative pressure device can be activated, as a result of which negative pressure is generated in the mixing chamber 1 relative to the component chamber 3. The pressure between the component chamber 3 having a higher pressure and the mixing chamber 1 having a lower pressure is equalized such that a pressure change, or a pressure reduction, takes place in the component chamber 3. With the equalization of the pressure, the rest of the second component 5 is conveyed by the feed line 8 into the mixing chamber 1. In the process, the second component also flows out of the interior of the component container 4 and out of the container head 10, which is held by the opening device with the opening downward, through the feed line 8 into the mixing chamber 1.

Figure 3:
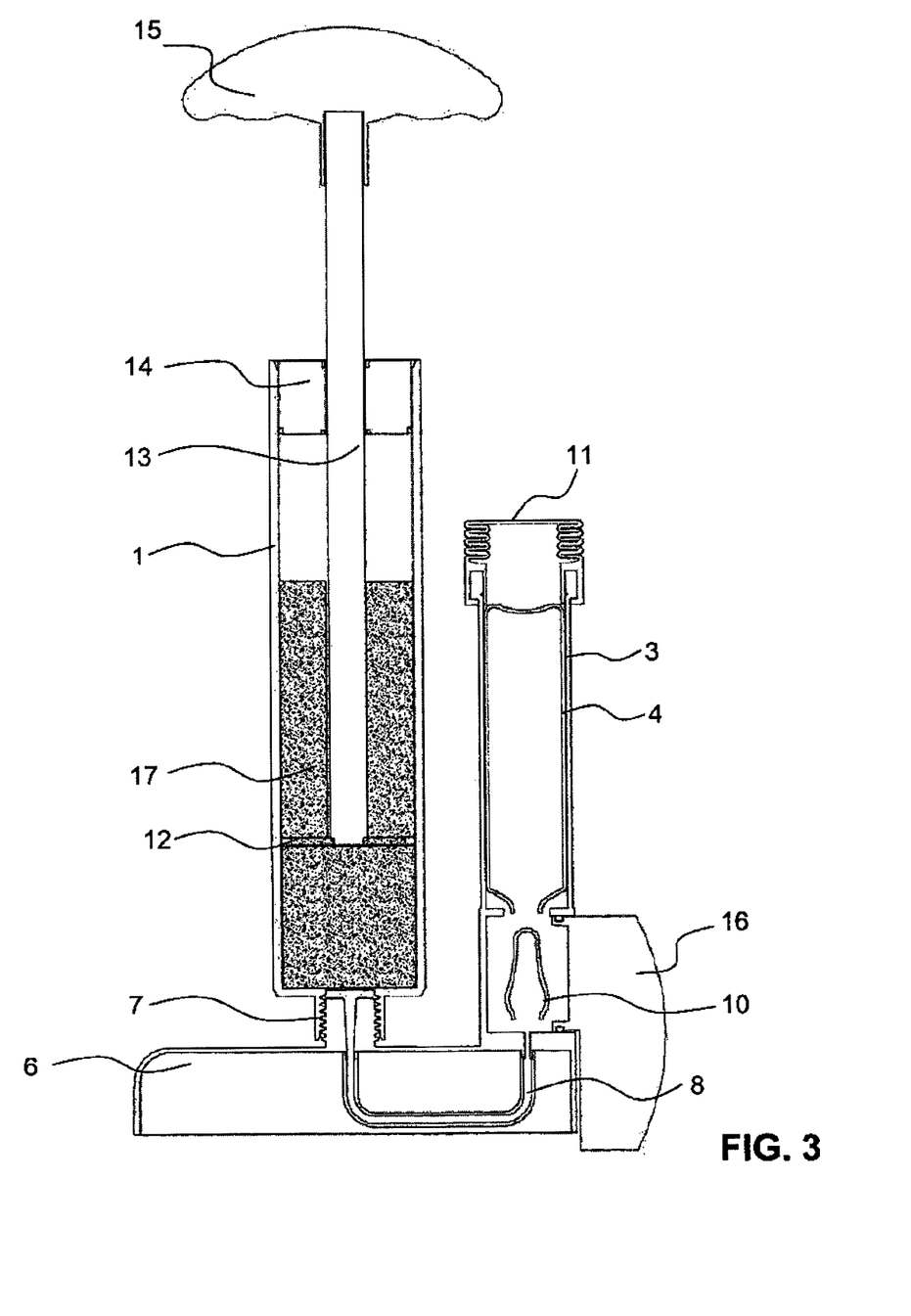
FIG. 3 shows a longitudinal section of the embodiment according to FIG. 1 in a display position.

In FIG. 3, the second component 5 has been completely transferred from the component chamber 3 into the mixing chamber. The negative pressure which is applied to the mixing chamber 1 by the negative pressure device, extends via the feed line 8 into the component chamber 3 and the bellows 11. Owing to the elastic properties of the bellows 11, the latter is compressed by the application of the negative pressure, in comparison to the ambient pressure, in the interior thereof.

The compression of the bellows serves as a display for the pressure change in the component chamber 3. By means of the compression of the bellows 11, the overall volume of the component chamber 3 is reduced.

The bellows may, for example, have a reddish coloring on the outside in the surfaces between the folds and a greenish coloring on the outside on the peaks of the folds and on the upper side of the bellows. In the expanded state of the bellows according to FIG. 1, the red surfaces between the folds are visible, and therefore the starting position is displayed. In the compressed state of the bellows, the red surfaces between the folds are covered by the folds being placed onto one another and only the greenish coloring provided at the peaks of the folds is visible, as a result of which the pressure change can be displayed.

The mixture 17 of the components 2 and 5 in the mixing chamber 1 can be produced by movement of the mixer 12 with the aid of the handle 15. The mixing chamber 1 can now be removed from the base unit 6. A discharge nozzle can subsequently be attached to the threaded connection part of the mixing chamber 1 and the mixture 17 can be discharged from the mixing chamber 1 in a known manner.

In an alternative procedure, a negative pressure can be applied in the mixing chamber 1 by means of the negative pressure device even before the component container 4 is opened. In this case, for example, the flexible lips 9 may serve as a closure device. In the starting position according to FIG. 1, the negative pressure device generates a negative pressure in the interior of the mixing chamber 1, in the feed line 8 and in that region of the component chamber 3 which lies in front of the flexible lips 9, or faces the feed line. In this case, a higher pressure (as a rule the ambient pressure) prevails in the component chamber 3 on the opposite side of the flexible lips 9, i.e. beyond the flexible lips, in the component container 4 and in the volume of the bellows 11. There is therefore a different pressure in front of and beyond the closure device in the form of the flexible lips present on the container head.

In FIG. 2, the closure device is in an open state, since the seal between the flexible lips 9 and the container head 10 has been eliminated by the container head 10 being severed from the component container 4. A pressure compensation can take place in the entire component container 4 and in the volume of the bellows 11, as a result of which the display apparatus is brought from a starting position into a display position.

Figure 4:
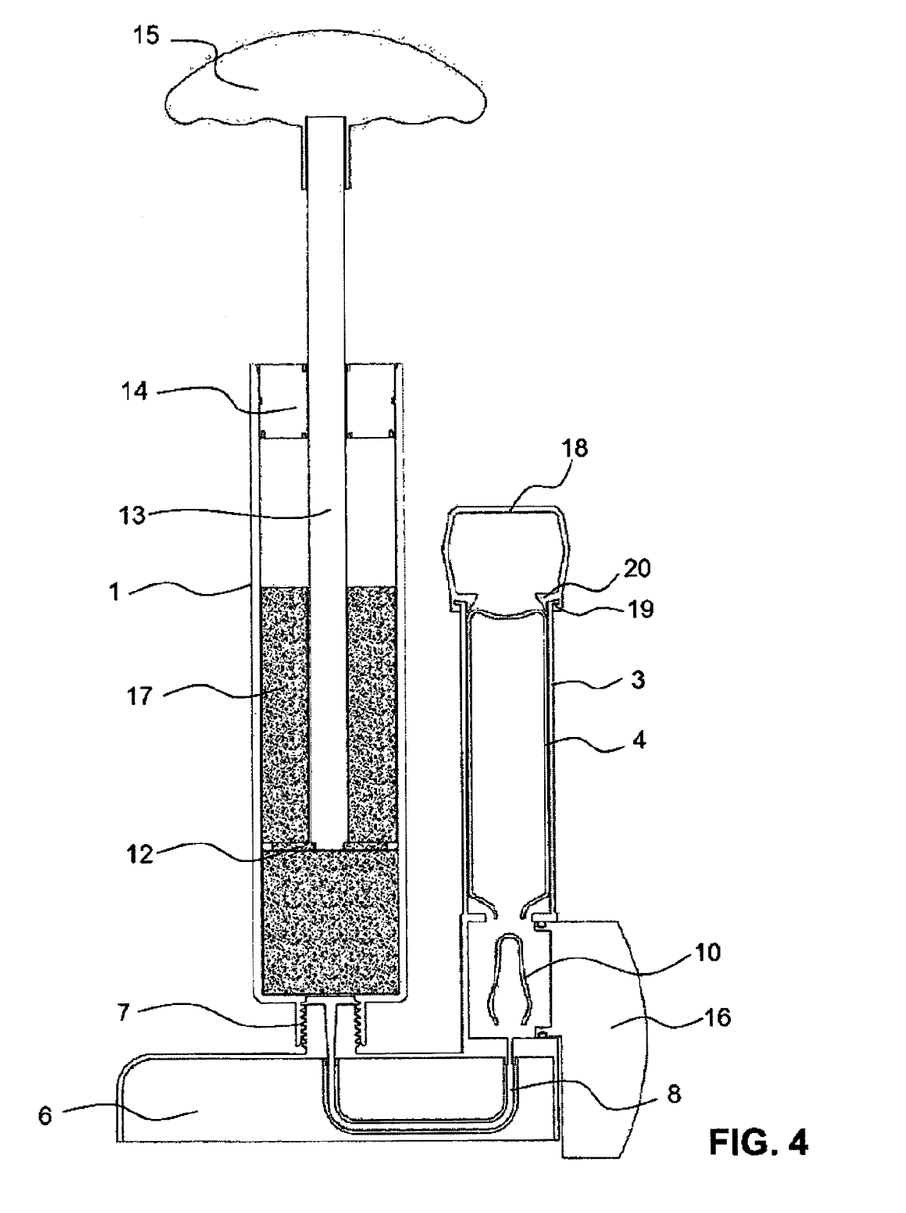
FIG. 4 shows a longitudinal section through a second embodiment of a mixing apparatus according to the present invention.

FIG. 4 shows a second embodiment of a mixing apparatus according to the present invention. The same components are provided with the same reference numbers. In this embodiment, a balloon bellows 18 is placed as display apparatus on the opening in the component chamber 3, which opening lies opposite the opening for the teed line 8. The balloon bellows 18 has an opening, on the circumference of which an outer sealing lip 19 and an inner sealing lip 20 are provided, between which the circumferential edge of the component chamber 3 comes to lie in the fitted state. In this case, the outer sealing lip 19 of the balloon bellows 18 adjoins the outside of the component chamber 3 and the inner sealing lip 20 adjoins the inside of the component chamber 3. A comparable fastening can also be provided for the expansion bellows 11. The balloon bellows 18 is of barrel-shaped design and is composed of elastic material such that the circumferential wall thereof can bend inward into the interior of the balloon volume. However, FIG. 4 shows the balloon bellows in an expanded state.

The mixing apparatus has been described with reference to the drawings and using various exemplary embodiments which essentially differ by means of a different configuration of the display apparatus for displaying a pressure change in the component chamber. In principle, however, the principle of the mixing apparatus according to the invention with a display apparatus for a pressure change in a component chamber can also include further embodiments. For example, a second component can be provided directly in the component chamber 3, in which case, for example, a valve in the feed line 8 can serve as the closure device. Furthermore, it is possible to provide the display apparatus at a different location on the component chamber 3, for example in a region of the circumferential wall of the component chamber. Furthermore, it is also possible to provide different opening mechanisms for opening a component container than those which are described in the abovementioned application WO 2010/012114 dated Jul. 14, 2009. Furthermore, the mixing chamber may also be formed without additional mixing elements, and therefore the components can be mixed, for example, by shaking of the mixing chamber. Finally, it is possible for more than one component chamber, preferably each having a display device, to be connected to the mixing chamber.

LIST OF REFERENCE NUMBERS

1 Mixing chamber
2 First component
3 Component chamber
4 Component container
5 Second component
6 Base unit
7 Screw connection
8 Feed line
9 Holding arms/flexible lips
10 Container head
11 Bellows
12 Mixer
13 Plunger rod
14 Stopper
15 Handle
16 Rotary lever
17 Mixture
18 Balloon bellows
19 Outer sealing lip
20 Inner sealing lip

The invention claimed is:

1. A mixing apparatus for mixing at least two components, the mixing apparatus comprising:
a mixing chamber with a first component,
at least one component chamber,
a feed line connecting the component chamber and the mixing chamber,
a closure device that is movable between a closed state in which the closure device blocks the feed line between the mixing chamber and the component chamber, and an open state in which the closure device opens the feed line between the mixing chamber and the component chamber,
an ampule containing a second component, the ampule being received in said component chamber, wherein the closure device is coupled to the ampule in the component chamber so as to open the ampule when the closure device is moved from the closed state to the open state,
a negative pressure device in order to generate a negative pressure in the mixing chamber so as to transport the second component from the component chamber through the feed line into the mixing chamber, and
a display apparatus which is provided on the component chamber in order to indicate a pressure change in the component chamber, the display apparatus comprising an elastic element connected to an opening of the component chamber.

2. The mixing apparatus as claimed in claim 1, wherein the display apparatus is designed to display a change in the volume of the component chamber.

3. The mixing apparatus as claimed in claim 1, wherein the display apparatus is designed to display a pressure reduction in the component chamber.

4. The mixing apparatus as claimed in claim 1, wherein the display apparatus is designed to display an emptying of the component from the component chamber.

5. The mixing apparatus as claimed in claim 1, wherein the component chamber has a first end at which the feed line is arranged, and wherein the component chamber has a second end which is opposite the first end and on which the display apparatus is arranged.

6. The mixing apparatus as claimed in claim 5, wherein the ampule with the second component is arranged in the component chamber between the feed line and the display apparatus.

7. The mixing apparatus as claimed in claim 1, wherein the display apparatus is movable counter to an elastic force from a starting position into a display position which differs therefrom.

8. The mixing apparatus as claimed in claim 1, wherein the display apparatus is arranged removably on the component chamber, the elastic element being pulled over an opening of the component chamber, an airtight connection between the component chamber and the display apparatus being formed by contraction of the elastic element.

9. The mixing apparatus as claimed in claim 7, wherein the display apparatus comprises a color marking for differentiation of the starting position from the display position by color.

10. The mixing apparatus as claimed claim 1, comprising a base unit, in which at least one part of the feed line is provided and which has connections for connecting the mixing chamber and the at least one component chamber to the feed line or to the part of the feed line, the mixing chamber and the component chamber being arranged side-by-side on the base unit.

11. The mixing apparatus as claimed in claim 5, wherein the elastic element projects away from the second end of the component chamber.

12. The mixing apparatus as claimed in claim 1, wherein the elastic element is an elastic bellows having a balloon-like or barrel-like shape or having an outer circumferential surface exhibiting a zigzag-like series of folds enabling the bellows to be compressed along a longitudinal direction.

13. The mixing apparatus as claimed in claim 1, wherein the elastic element is an elastic bellows that is shaped like a barrel, the barrel defining an interior and having a circumferential sidewall configured to bend inward towards the interior of the barrel when a negative pressure is applied to the component chamber.

14. The mixing apparatus as claimed in claim 1, wherein the ampule has an ampule body and a severable ampule head, and wherein movement of the closure device from the closed state to the open state causes the ampule head to be severed from the ampule body, and further causes the feed line between the mixing chamber and the component chamber to be opened, so as to allow the second component to exit the ampule and to flow from the component chamber through the feed line to the mixing chamber.

15. The mixing apparatus as claimed in claim 1, wherein the closure device comprises a rotary lever arranged on the component chamber and outside of the component chamber, and wherein the closure device is configured to be moved from the closed state to the open state by rotation of the rotary lever.

16. The mixing apparatus as claimed in claim 15,
wherein the component chamber has a first end at which the feed line is arranged,
wherein the component chamber has a second end which is opposite the first end and on which the display apparatus is arranged, the ampule being arranged in the component chamber between the first end and the second end thereof, and
wherein the rotary lever is rotatable about an axis that is perpendicular to a longitudinal direction extending from the first end to the second end.

17. The mixing apparatus as claimed in claim 1, further comprising:
a mixer that is movably arranged in the mixing chamber;
a plunger rod that is connected to the mixer and that is arranged in the interior of the mixing chamber so as to be movable in the longitudinal direction of the mixing chamber, the plunger rod protruding out of the mixing chamber;
a handle attached to the plunger rod outside of the mixing chamber for sliding and rotating the plunger rod; and
a stopper that closes off the mixing chamber at a first end thereof, the plunger rod of the mixer being guided in the stopper;
the mixing chamber having an opening to which the feed line is connected, the opening being provided at a second end of the mixing chamber that is opposite to the first end.

* * * * *